(12) United States Patent
de Vries et al.

(10) Patent No.: US 8,257,388 B2
(45) Date of Patent: *Sep. 4, 2012

(54) SURGICAL INSTRUMENT AND METHOD

(75) Inventors: Luc de Vries, AB Diepenheimthe (NL); Wouter van Furth, BG Hilversum (NL); Eric Windeler, Kenilworth, IL (US)

(73) Assignee: Sutureaid Holdings B.V., Ede (NL)

( * ) Notice: Subject to any disclaimer, the term of this patent is extended or adjusted under 35 U.S.C. 154(b) by 710 days.

This patent is subject to a terminal disclaimer.

(21) Appl. No.: 11/025,727

(22) Filed: Dec. 29, 2004

(65) Prior Publication Data

US 2005/0222612 A1    Oct. 6, 2005

(30) Foreign Application Priority Data

Mar. 31, 2004    (NL) ...................................... 1025852

(51) Int. Cl.
*A61B 17/50*    (2006.01)
*B25B 9/02*    (2006.01)

(52) U.S. Cl. ..... 606/210; 606/148; 294/99.2; 223/109 R
(58) Field of Classification Search ................. 606/148, 606/151, 205–208, 210, 211, 213–217, 222–227, 606/107; 294/99.2, 1.2; 223/109 R; 433/39, 433/157–159, 162, 265

See application file for complete search history.

(56) References Cited

U.S. PATENT DOCUMENTS

| | | | |
|---|---|---|---|
| 1,359,164 A | 11/1920 | Giudice et al. | |
| 2,087,372 A * | 7/1937 | Crawford | 66/117 |
| 2,504,202 A | 4/1950 | Kadavy et al. | |
| 2,743,726 A * | 5/1956 | Grieshaber | 606/207 |
| 3,349,772 A * | 10/1967 | Rygg | 606/145 |
| 3,728,739 A * | 4/1973 | Semp | 2/168 |
| 3,878,848 A * | 4/1975 | Hiebert | 606/148 |
| 3,946,740 A | 3/1976 | Bassett | |
| 4,561,574 A * | 12/1985 | Brown | 223/109 R |
| 4,821,719 A | 4/1989 | Fogarty | |
| 4,955,896 A * | 9/1990 | Freeman | 606/210 |
| 5,047,049 A * | 9/1991 | Salai | 606/205 |
| 5,334,215 A * | 8/1994 | Chen | 606/210 |
| 5,342,375 A | 8/1994 | Lemole | |

(Continued)

FOREIGN PATENT DOCUMENTS

DE    759 986    3/1953

(Continued)

OTHER PUBLICATIONS

International Search Report—PCT/EP2005/003476.

(Continued)

*Primary Examiner* — Kathleen Sonnett
(74) *Attorney, Agent, or Firm* — Morgan, Lewis & Bockius LLP

(57) ABSTRACT

A surgical instrument, e.g. forceps, and method to be used for suturing tissue are provided, the surgical instrument comprising a first arm and a second arm that are spring-connected at a proximal end, while at a distal end the first arm and the second arm can be moved towards each other, and wherein at least the first arm and/or the second arm can be provided with a bullet that is suitable for receiving and affixing a surgical needle, wherein the bullet is designed for being positioned at the distal end, at an inside and/or lower side of the end of an arm.

4 Claims, 17 Drawing Sheets

U.S. PATENT DOCUMENTS

| | | | |
|---|---|---|---|
| 5,405,353 A | 4/1995 | Randall | |
| 5,487,749 A | 1/1996 | Smith | |
| 5,490,858 A | 2/1996 | Shuter | |
| 5,556,403 A * | 9/1996 | Michalos | 606/148 |
| 5,618,303 A | 4/1997 | Marlow et al. | |
| 5,645,552 A | 7/1997 | Sherts | |
| 5,797,537 A | 8/1998 | Oberlin et al. | |
| 5,814,069 A | 9/1998 | Schulze et al. | |
| 5,824,009 A * | 10/1998 | Fukuda et al. | 606/144 |
| 5,897,571 A | 4/1999 | Kazama | |
| 6,059,776 A | 5/2000 | Gatto | |
| 6,099,539 A | 8/2000 | Howell et al. | |
| 6,206,896 B1 | 3/2001 | Howell et al. | |
| 6,322,570 B1 * | 11/2001 | Matsutani et al. | 606/145 |
| 6,387,106 B1 | 5/2002 | Howell et al. | |
| 6,494,860 B2 | 12/2002 | Rocamora et al. | |
| 6,551,329 B1 | 4/2003 | Kortenbach et al. | |
| 6,989,017 B2 | 1/2006 | Howell et al. | |
| 2002/0107482 A1 | 8/2002 | Rocamora et al. | |
| 2003/0004523 A1 | 1/2003 | Chan et al. | |
| 2003/0045833 A1 * | 3/2003 | Murdoch | 604/110 |
| 2003/0208100 A1 | 11/2003 | Levy | |
| 2005/0125013 A1 * | 6/2005 | Kessler | 606/148 |
| 2005/0228441 A1 | 10/2005 | Wood et al. | |
| 2007/0087602 A1 | 4/2007 | Smith et al. | |
| 2007/0135824 A1 | 6/2007 | O'Brien | |

FOREIGN PATENT DOCUMENTS

| | | |
|---|---|---|
| DE | 759986 | 3/1953 |
| EP | 0 351 165 | 1/1990 |
| EP | 1762188 | 3/2007 |
| FR | 2 474 303 | 7/1981 |
| GB | 2396110 | 6/2004 |
| JP | 08-033635 A | 2/1996 |
| JP | 11-216145 A | 8/1999 |
| JP | 2003-210486 | 7/2003 |
| WO | WO 2005/094698 A3 | 9/1981 |
| WO | 94/16628 | 8/1994 |
| WO | 99/11179 | 3/1999 |
| WO | WO 02/068034 A2 | 9/2002 |
| WO | WO 02096312 A2 * | 12/2002 |

OTHER PUBLICATIONS

European Search Report of EP 08100511 dated Sep. 9, 2008.

International Preliminary Report on Patentability of PCT/EP20005/003476 dated Jul. 4, 2006.

Communication Relating to the Results of the Partial International Search of PCT/EP2009/050811 dated May 13, 2009.

Japanese Patent Office, Notice of Reasons for Rejection, Japanese Patent Application No. 2007-505515, mailed Jan. 20, 2011.

* cited by examiner

SURGICAL INSTRUMENT AND METHOD

The present application claims priority from Dutch patent application NL 1025852, filed 31 Mar. 2004.

FIELD OF THE INVENTION

The invention relates to a surgical instrument to be used for suturing tissue while reducing the possibility of needle perforation accidents.

BACKGROUND

Standard suturing instruments and techniques present significant risks to both patient and surgeon by way of possible glove perforation accidents in which a suture needle penetrates the surgeon's glove. Such perforation accidents may allow pathogenic organisms such as, but not limited to, the hepatitis virus B, the hepatitis virus C and the human immunodeficiency virus (HIV) to be transmitted from the patient to the practitioner.

Conversely, a perforation accident may cause a break in the sterile barrier between practitioner and patient, which increases the risk of the patient's wound becoming infected.

One approach to help avoid this problem involves the use of surgical forceps of the kind described in U.S. Patent Application US 2003/0045833 A1. The surgical forceps described in that application has near the distal end at the outside of an arm of the forceps a flexible material that can be used for manipulating a surgical needle during suturing in order to attempt to prevent needle perforation accidents.

Among the drawbacks of these and other surgical forceps is that when suturing using a surgical needle and a suture attached thereto, the tissue may sustain damage. This is a particular liability where delicate tissue is concerned through which it is difficult to pass the surgical needle without causing tissue damage. The point of the surgical needle initially pushes the tissue forward to subsequently lance it, which causes damage to the tissue. Moreover, in the surgical forceps described in the above application, the placement of the flexible material requires that the instrument be pushed further into the wound thereby increasing the likelihood of damaging the tissue and/or previously tied sutures.

Thus, there remains a need for suturing forceps, which minimize the risk of glove perforation accidents and tissue damage.

SUMMARY OF THE INVENTION

The present invention is directed to a surgical instrument (suturing forceps) useful in conventional surgery, endoscopic and robotic surgery. The instrument comprises a first arm and a second arm that are connected at a proximal end (optionally spring-connected) so as to bias the arms in an open configuration and which define a space between them which can be reduced or increased. At a distal end, the arms can be moved towards each other thereby reducing the space between the arms. The instrument further comprises a surgical needle-receiving and affixing portion herein referred to as a "bullet" at the distal end of at least the first arm and/or the second arm, at an inside and/or lower side of the distal end of an arm. The bullet may be removable from the instrument.

The invention is further directed to the forceps described above comprising an arm manipulating means by which one arm of the instrument, preferably the arm lacking the bullet may move away from the surgical field during the suturing procedure. Specifically, the manipulated arm is removed from the path defined by the movement of the surgical needle during suturing, which is itself defined by the curvature of the needle. Such manipulation of an arm avoids contact with the tissue being sutured thereby preventing tissue damage and facilitating the suturing process.

This may be accomplished using a variety of means including, for example, using a hinge mechanism fixed at the proximal or distal end of at least one arm of the instrument, as described in more detail below. The bullet can be placed at the distal end of the first arm and/or at the distal end of the hinge mechanism. The hinge is designed to provide a means for drawing the distal end of one of the arms away from the surgical field (preferably the arm opposite the bullet) as the distance between the distal ends of the arms increases. Conversely, as the distance between the distal ends of the arms decreases, the distal end of the arm acted upon by the hinge mechanism extends so that the arms become of similar length as the distal ends of the arms make contact with each other.

The invention is further directed to a method for suturing tissue using the instrument of the present invention comprising the steps of 1) securing and supporting a first area of tissue to be sutured with the distal ends of the instrument, 2) securing a surgical needle and a suture material attached thereto with a needle holding tool, 3) piercing the first area of tissue to be sutured with the needle using the bullet to support the tissue, 4) passing the needle through the tissue into or onto the bullet, 5) releasing the needle from the needle holding tool, 6) releasing the first area of tissue secured by the distal ends of the instrument, 7) guiding the affixed needle with the instrument following the curvature of the needle, 8) removing the needle from the bullet with the needle holding tool, and 9) repeating steps 1-8 on a second area of tissue to be sutured to the first area of the lesion whereupon the suture passing through the first and second areas of tissue is tied in a knot. Alternatively, prior to the bullet receiving and affixing the surgical needle, the surgical needle in one movement may pierce the first and second areas of tissue to be sutured. The suture is knotted by a force applied by the needle holding tool pulling on the end of the suture and a second pulling force applied by the instrument to which the surgical needle is affixed.

BRIEF DESCRIPTION OF THE DRAWINGS

The invention will now be further elucidated by way of exemplary embodiments that form no limitation to the appended claims, and with reference to the following drawings.

In the drawings.

DETAILED DESCRIPTION OF THE INVENTION

The invention is directed to a surgical instrument (suturing forceps), with which needle perforation accidents can be avoided, tissue damage during suturing can be reduced and which allows suturing to be performed more easily.

The following description is made by way of example and is not intended to limit the invention as set out in the appended claims.

The forceps of the present invention comprises at least a first and second arm that are connected at one end and which may be biased, for example, by a spring means, in an open position and which defines a space between them which can be reduced or increased. The instrument also comprises a needle receiving and affixing bullet that is preferably positioned at the distal end, at an inside and/or lower side of the end of an arm. The term "open" in the context of the present invention refers to the position wherein the distal ends of the two arms are apart. The term "closed" refers to the position wherein the distal ends of the two arms are in close proximity or touching. The term "form lock" refers to the properties of a bullet embodiment whereby the deformation of a bullet that is pierced by a surgical needle results in a pressure exerted on the surgical needle from the resistance of the bullet to return to its original form thereby affixing (locking) the surgical needle to the bullet.

When suturing tissue using a suture and surgical needle, the forceps of the present invention makes it possible to control the suturing process in such a manner that immediately after the point of the surgical needle has pierced the tissue, it is able to pass into the bullet where it is retained until removal by the surgeon, preferably with the use of a surgical needle holder. This allows the surgical needle to be manipulated safely during suturing without touching the needle with the hands, thereby reducing the possibility of needle perforation accidents.

The bullet also provides support for the portion of tissue being sutured by using the forceps of the present invention to effectively avoid tissue damage because the bullet provides a counter pressure against the pressure of the needle supporting the tissue to be sutured thereby minimizing tissue stretch. Furthermore, the suturing operation can be continued using the forceps to manipulate the needle, without the necessity of either manually touching the needle or using a needle holding instrument.

Figure 8:
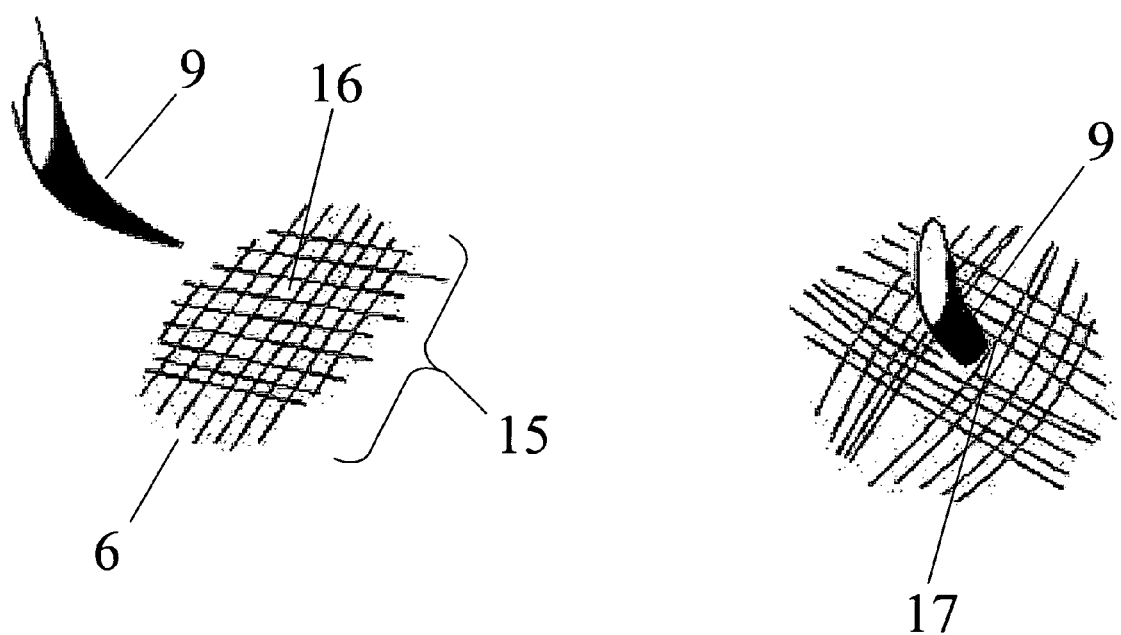
FIG. 8 shows a diagram illustrating the wire mesh embodiment of the bullet.
Figure 9:
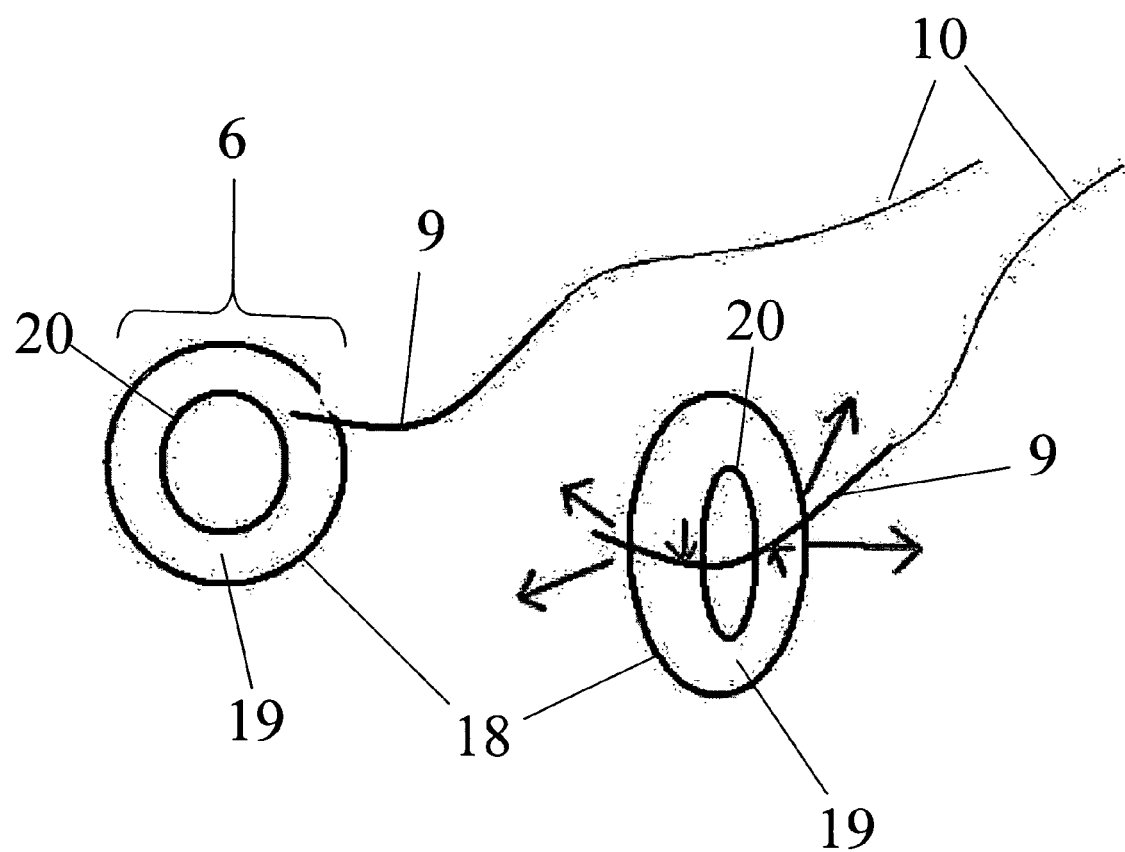
FIG. 9 shows a diagram illustrating the form lock embodiment of the bullet.

The bullet may be comprised of any material or designed in any way such that it is capable of receiving and removably affixing or retaining a surgical needle. For example, the material may be pierceable such as synthetic rubber or wire mesh. An example of a bullet comprised of wire mesh is illustrated in FIG. 8. The bullet may also be comprised of a hollow synthetic material such that when penetrated, the pressure of the needle penetrating the first wall of the bullet deforms the bullet, and this pressure, together with the pressure created by the penetration and subsequent deformation of the second wall creates significant pressure on the needle creating a "form lock," enhancing the bullet's grip on the needle. An example of the form lock embodiment of the bullet is illustrated in FIG. 9. Alternatively the hollow space may be filled with a substance such as a gel that may contribute to "locking" a surgical needle. The bullet may also be comprised of a material with magnetic properties suitable for receiving and retaining a surgical needle or any other receiving and retaining means as with an adhesive. Other mechanical means may also be used to receive and removably affix a needle. For example, the bullet may be designed with an opening that allows a surgical needle to be inserted frictionlessly into the bullet such that when the distal ends of the arms are apart, a plunger mechanism which is dependent on the distance between the distal ends of the arms is activated and pushes on the part of the needle that is through the opening. The pushing force of the plunger acts as a guillotine and results in a grip on the needle thereby affixing the needle to the bullet. Conversely, when the distal ends of the arms are in close proximity, the plunger mechanism responds by retracting the plunger, removing the pressure on the needle, and the needle is released. Alternatively, the plunger mechanism may be independent of the distance between the distal ends of the forceps and may be activated manually by the surgeon. The bullet may also be comprised of a substance, for example, a soft gel, that receives a surgical needle and applying a change in temperature at the site of the bullet, for example by using a laser, causes it to harden thereby fixing the surgical needle that can be released by again applying change in temperature at the site of the bullet. The bullet of the above-mentioned embodiments may be comprised of a biodegradable material in the event that if any part of the bullet falls into the wound, no additional harm would be caused to the patient, as the bullet would harmlessly dissolve in the body.

Figure 10:
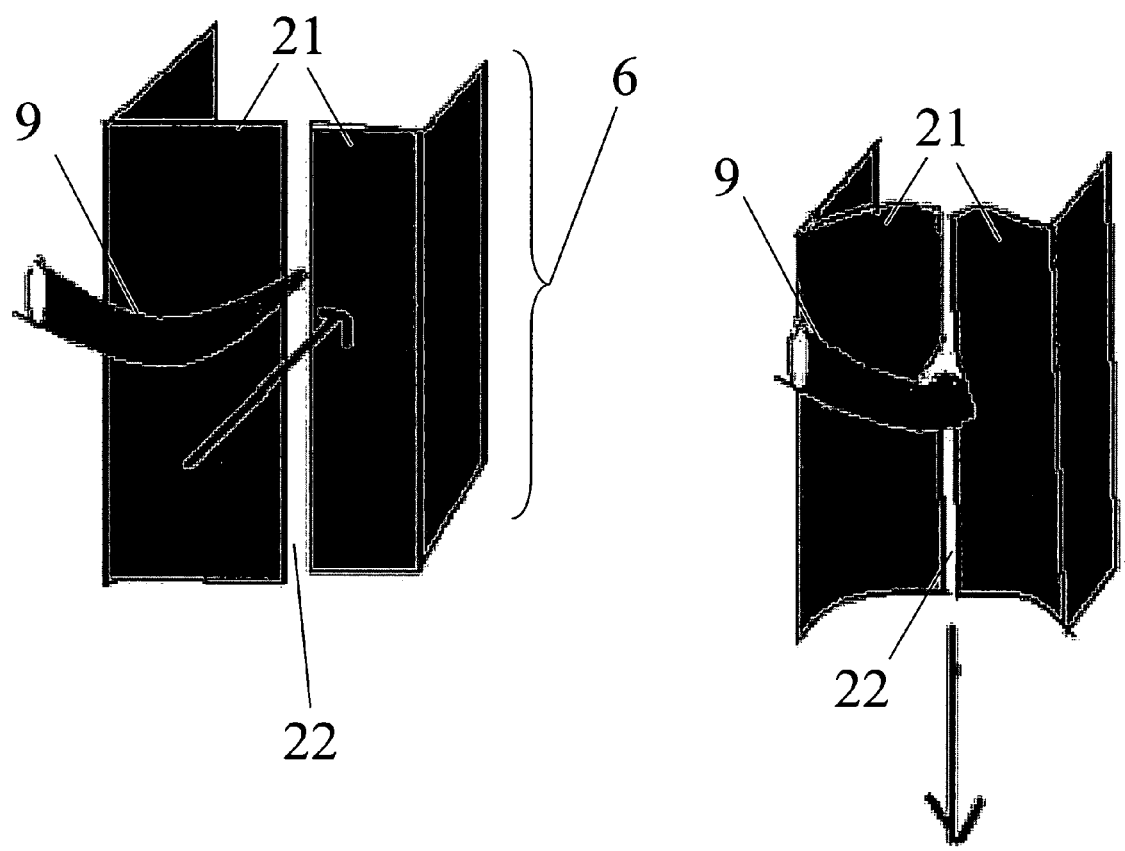
FIG. 10 shows a diagram illustrating the saloon doors embodiment of the bullet.

The bullet may also be designed to have a narrow slit into which a surgical needle is guided such that when the forceps are manipulated to pull on the needle, flaps of the slit close thereby affixing the needle to the bullet. The needle is released by pulling or pushing it in the direction of the flaps thereby opening the flaps. Such an embodiment may be referred to as a "saloon door" mechanism. An example of this embodiment is illustrated in FIG. 10.

In a further aspect of the invention, the bullet may be "loaded" with an electric or other charge or with receptors to guide the needle to the bullet such that the needle is controlled and gripped more easily.

In a further aspect of the invention the bullet is provided on a holder that is detachably placed on at least one arm as exemplified herein. The holder with the bullet may thus be a disposable component that can be supplied sterile, while the forceps upon which the holder is placed may be retained and sterilized from case to case. The holder with the bullet is designed to be removably placed on forceps of the kind illustrated in FIG. 3.

In using the present invention there is a moment in suturing in which the surgeon pulls the needle (that is already fixed in the bullet) through the tissue. In order to do so without harming the tissue, the surgeon guides the forceps following the curvature of the needle. By doing so, the arm opposite to the arm with the bullet to which the needle is affixed can touch or even get stuck in the tissue. Providing a means for moving the opposite arm away from the surgical field when the distal ends of the two arms are apart alleviates this problem.

Figure 12:
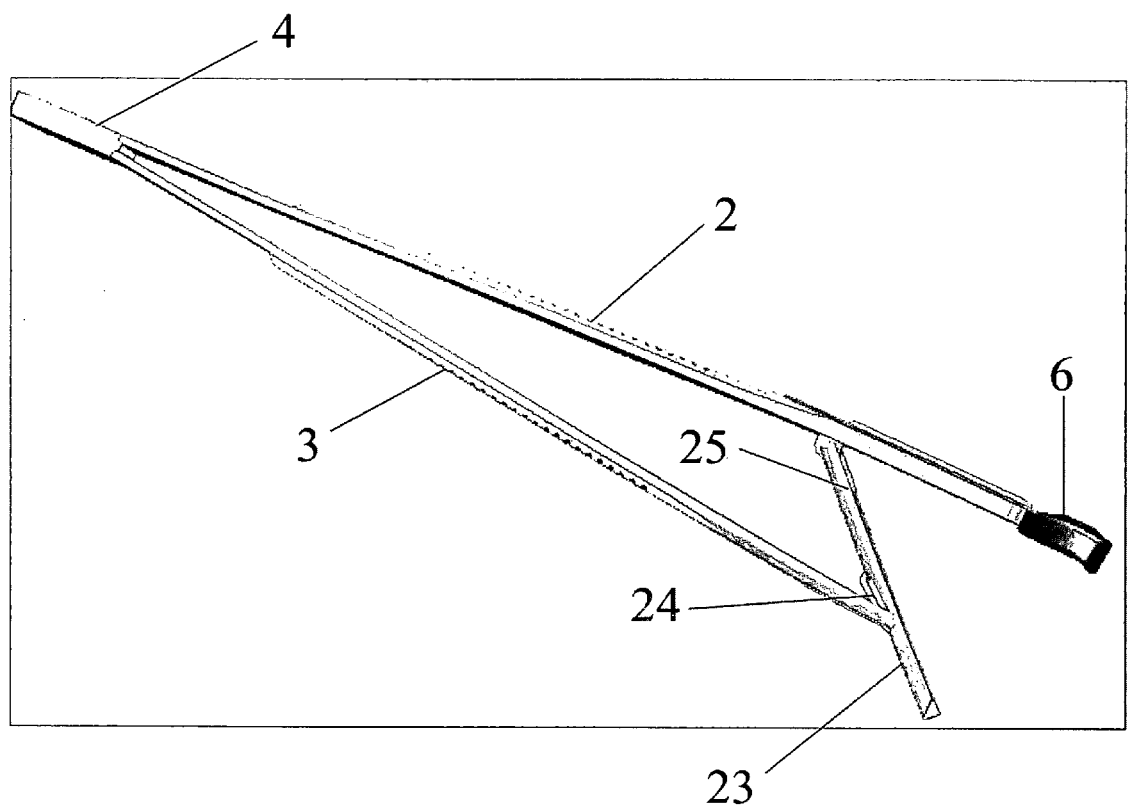
FIG. 12 shows a perspective view of the preferred embodiment of the surgical forceps with a double hinge mechanism in the open position.

To this end, a preferred embodiment of the invention is comprised of the two arms of the forceps being of unequal length with a hinge mechanism, which is comprised of a hinge and a lever, attached to the shorter arm that is opposite the bullet. When the forceps are in a closed position, the distal end of lever extends to contact the distal end of the arm to which the bullet is attached. When in the open position, the lever retracts and is no longer in the way of making a circular motion with the forceps to pull the needle through the tissue along the curvature of the needle. Such an embodiment may be referred to as "double-hinge." An example of this embodiment is illustrated in FIG. 12.

Figure 11:
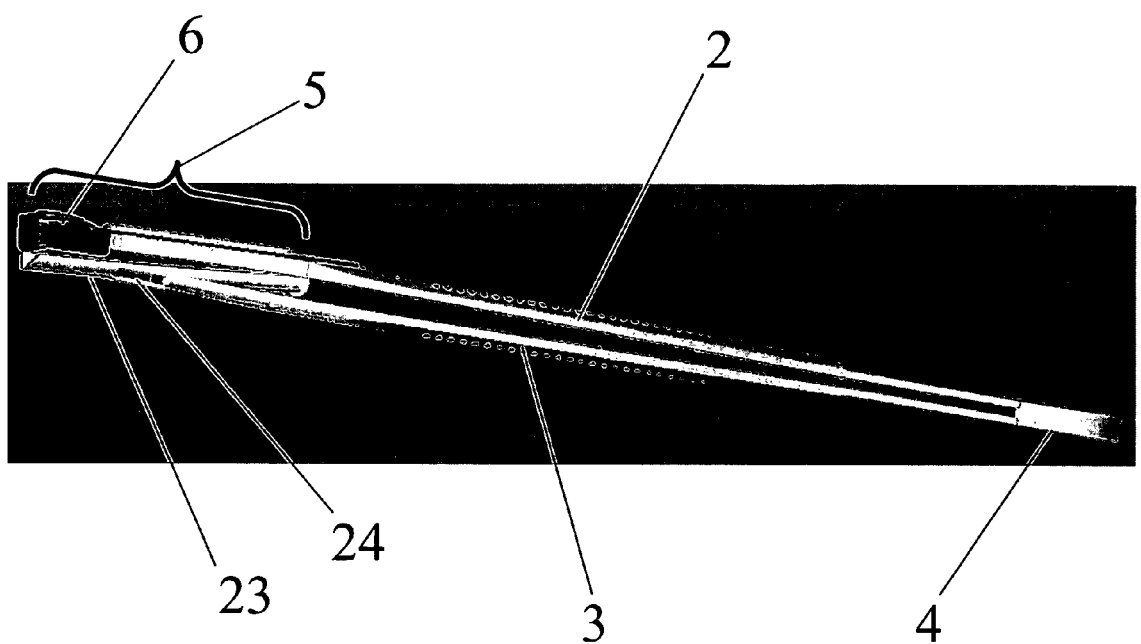
FIG. 11 shows a perspective view of the preferred embodiment of the surgical forceps with a double hinge mechanism in the closed position.
Figure 13:
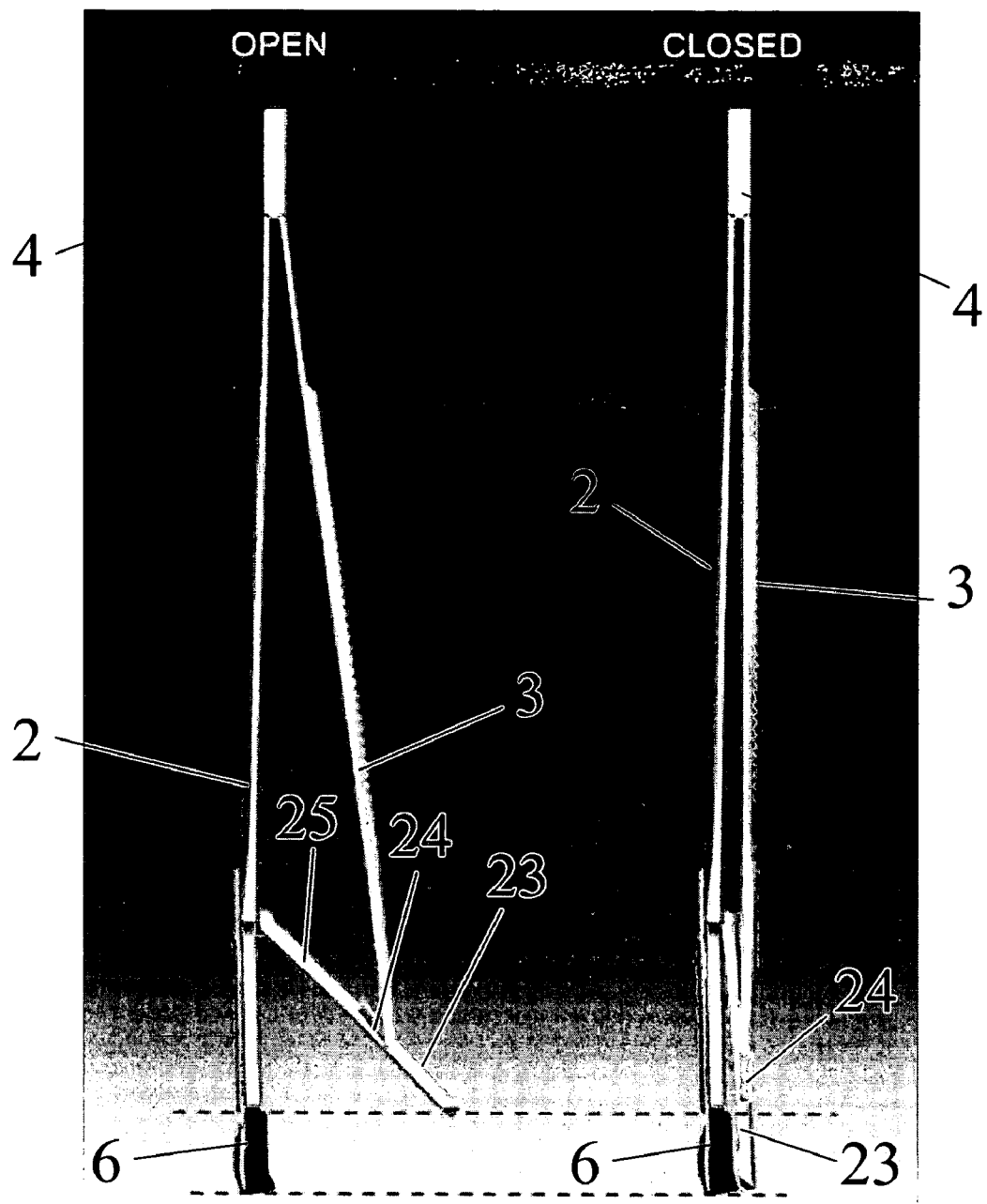
FIG. 13 shows perspective views of the preferred embodiment of the surgical forceps with a double hinge in both open and closed positions.

For this embodiment, the hinge mechanism is comprised of a hinge that is medially fixed to a lever. The hinge is also fixed at the distal end of the shorter arm opposite the bullet such that the distal end of the lever acts as an extension of the shorter arm. The proximal end of the lever is slidably disposed along the inside of the longer arm. Examples of this embodiment are illustrated in FIGS. 11, 12 and 13.

Figure 14:
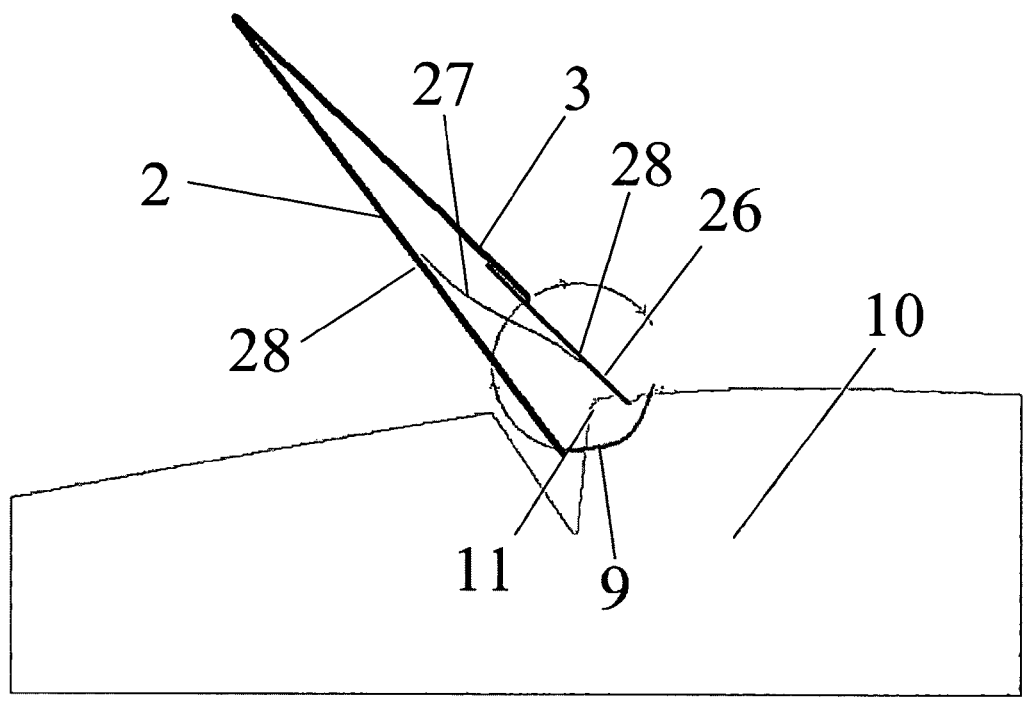
FIG. 14: shows a diagram illustrating the spring enforced sliding arm embodiment of the surgical forceps.
Figure 14:
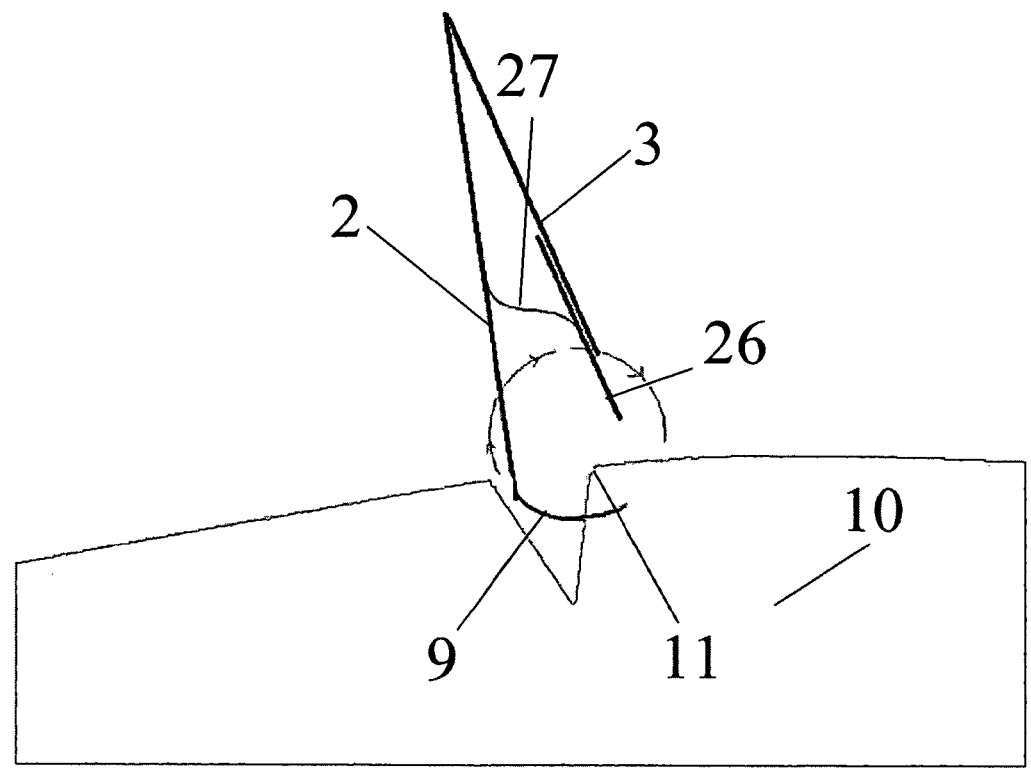

In an alternate embodiment of the invention, the hinge mechanism is in the form of a spring medially fixed to a sliding lever. The spring opens the forceps and by motion of the sliding lever makes the distal end of the arm that is to be moved away (i.e. the arm opposite the arm with the bullet) slide in the proximal direction when the forceps are open. When the forceps are closed, the sliding lever slides towards the distal end of the forceps to enable sufficient grip of the tissue. Such an embodiment may be referred to as "spring enforced sliding arm." An example of this embodiment is illustrated in FIG. 14.

Figure 15:
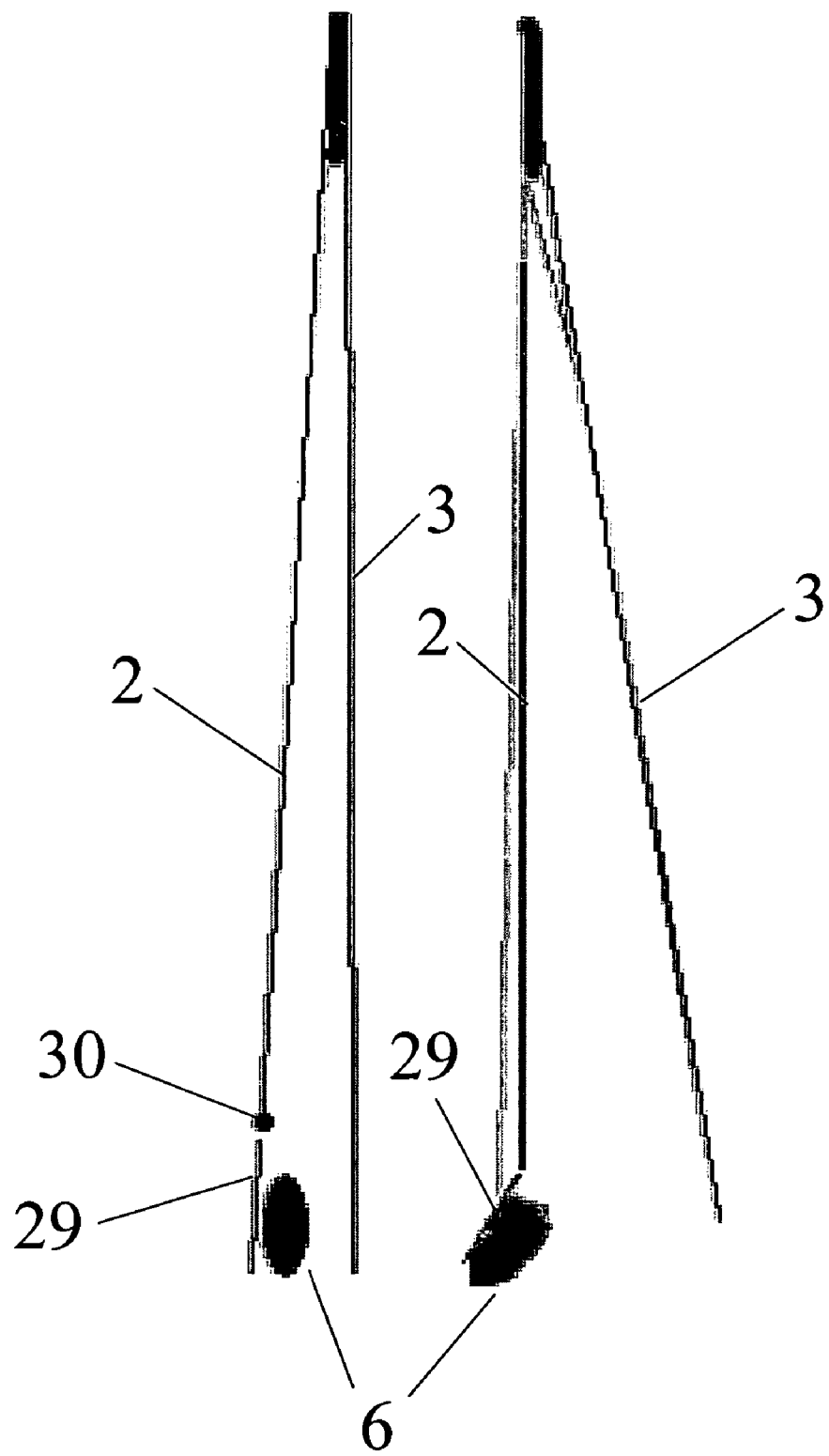
FIG. 15 shows a diagram illustrating the flipping bullet embodiment of the surgical forceps.

In an alternate embodiment of the invention, the hinge mechanism is fixed to the distal end of the shorter arm of the forceps. Furthermore, the bullet is placed at the distal end of the hinge mechanism. Spring-forced movement of the hinge flips it away from the longer arm of the forceps and allows the surgeon to pull the surgical needle through, along the natural needle path, without damaging the tissue. Such an embodiment may be referred to as "flipping bullet." An example of this embodiment is illustrated in FIG. 15.

Figure 16:
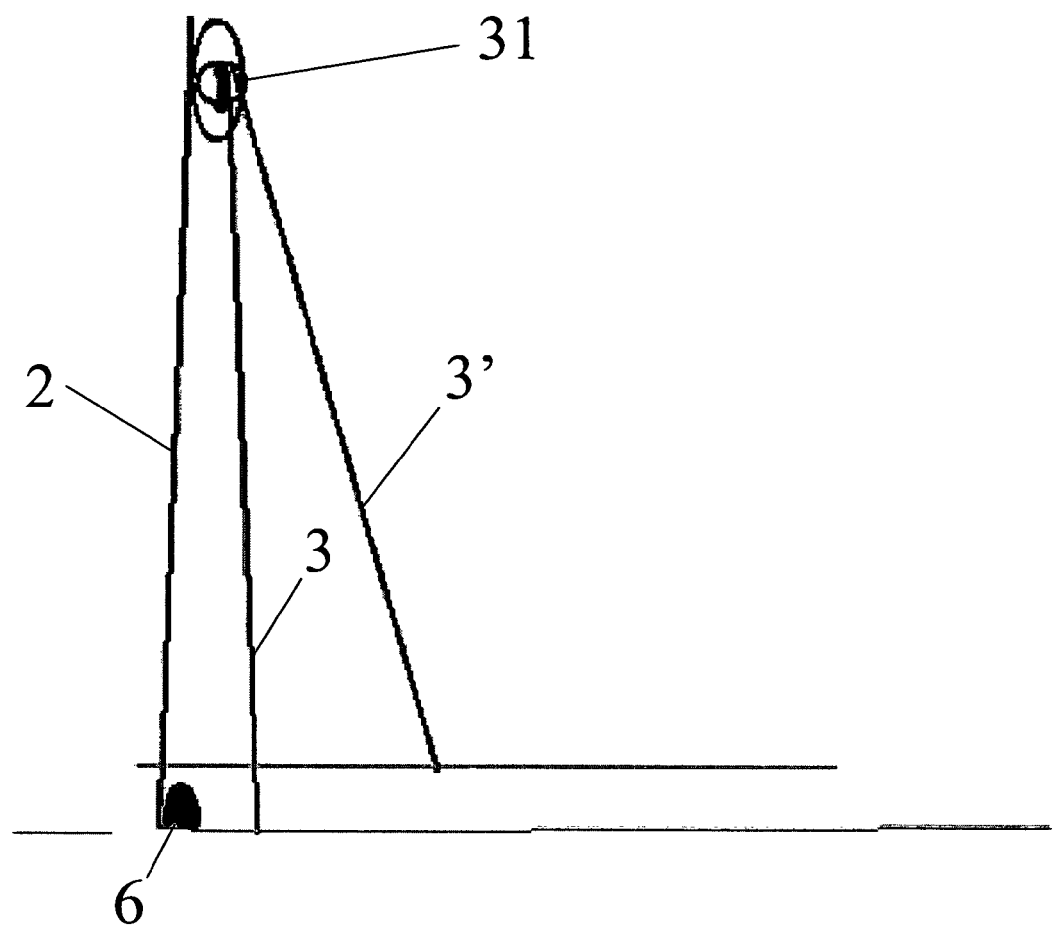
FIG. 16 shows a diagram illustrating the accentric axis embodiment of the surgical forceps.

In an additional embodiment of the invention, an elliptical hinge mechanism at the proximal end of the forceps may be used in which the point of rotation in the proximal end makes a translating movement at the same time as the rotating movement takes place. This design "shortens" the arm that is opposite the bullet when the forceps are opened. Such an embodiment may be referred to as "accentric axis." An example of this embodiment is illustrated in FIG. 16.

Figure 17:
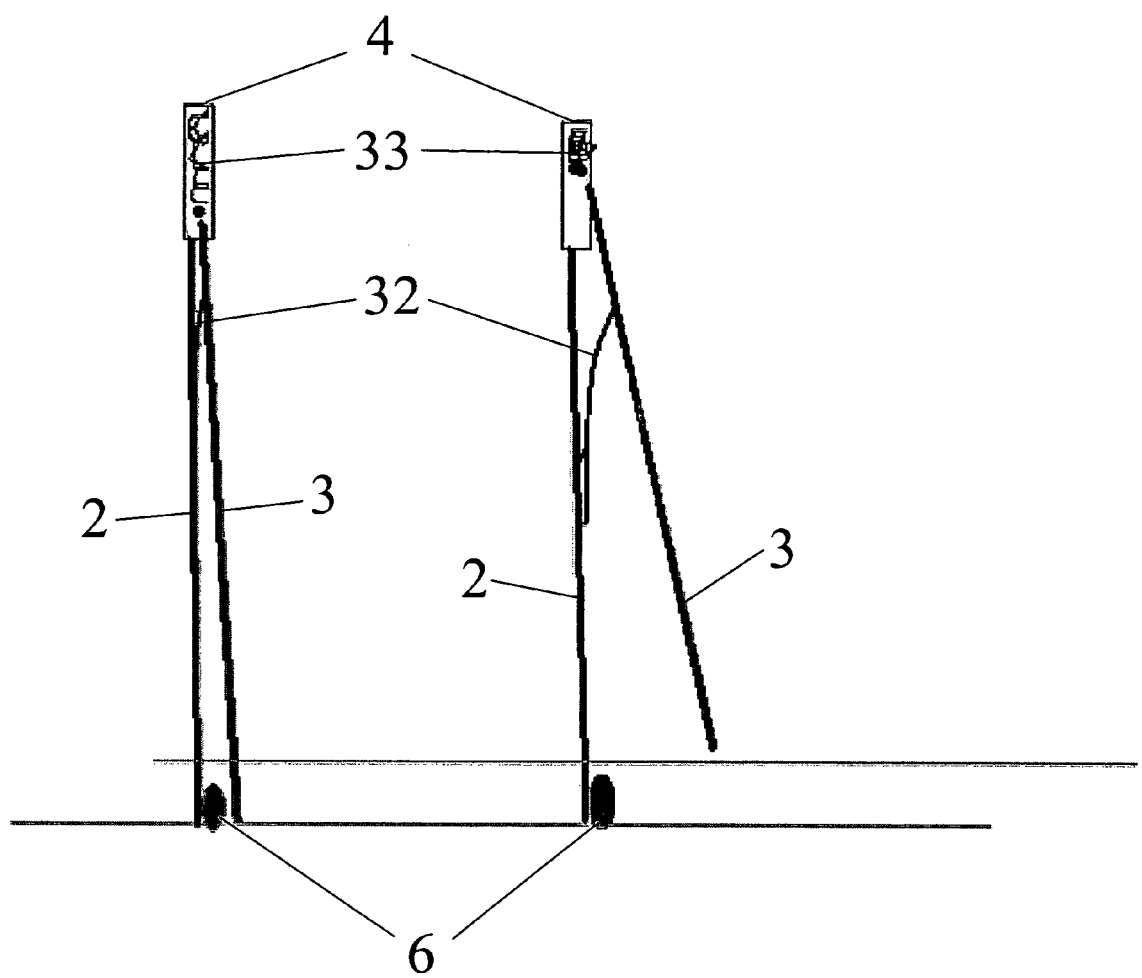
FIG. 17 shows a diagram illustrating the double spring embodiment of the surgical forceps.

In an additional embodiment of the invention, the hinge mechanism is comprised of a double spring. A first spring holds the two arms apart in the open position in which the arm opposite that which holds the bullet is shorter. When the first spring is engaged and the distal ends of the two arms are brought together, a second spring located at the proximal end of the instrument and fixed to the shorter arm is also engaged and extends the shorter arm such that the distal ends of the two arms meet when the forceps are in the closed position. Such an embodiment may be referred to as "double spring." An example of this embodiment is illustrated in FIG. 17. Other means by which to accomplish shortening of the arm of the forceps will be readily apparent to one of ordinary skill in the art.

Identical reference numerals used in the figures refer to similar parts.

Figure 1:
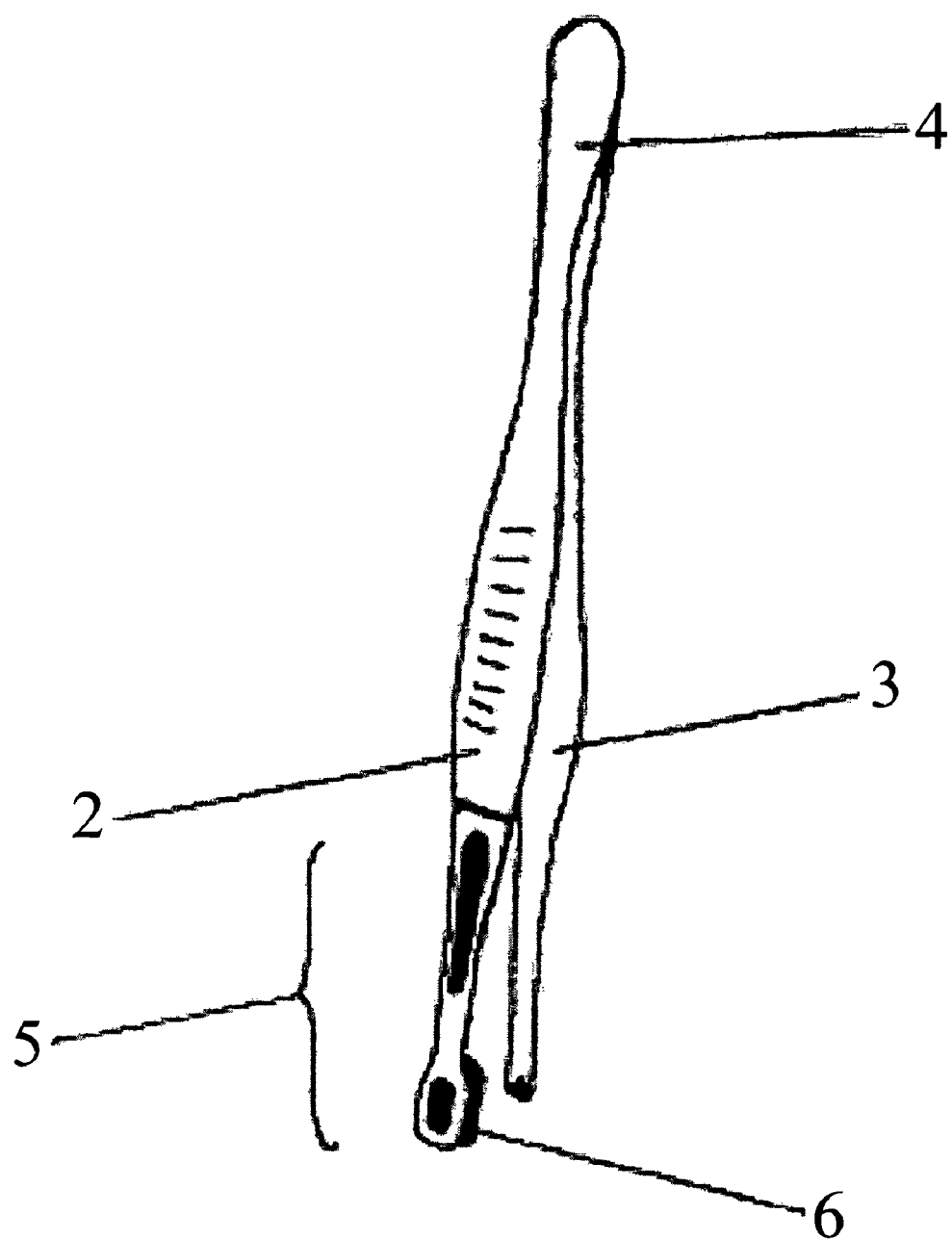
FIG. 1 shows a perspective view of a surgical instrument according to the invention.

Referring first to FIG. 1, where reference numeral 1 indicates the surgical forceps according to the invention.

These surgical forceps 1 are suitable to be used for suturing tissue and comprise a first forceps arm 2 and a second forceps arm 3, spring-connected at a proximal end 4, i.e. the end which during the manipulation of the forceps 1 lies in the hand and which arms define a space between them which an be reduced and increased.

At a distal end 5, the first forceps arm 2 and the second forceps arm 3 can be moved toward each other.

FIG. 1 further shows that the first forceps arm 2 is provided with a bullet 6. This bullet 6, in its preferred embodiment, is comprised of a needle receiving and retaining material such an elastomeric material which is suitable to be pierced with a surgical needle and which removably retains the needle until removed by the surgeon, as will be further explained below.

The bullet may also be provided on the second arm 3 or, as the case may be, only on the second arm 3. Within the framework of the invention, however, at least one of the forceps arms 2, 3 must be provided with a bullet 6.

As FIG. 1 shows, the bullet 6 is positioned close to or at the distal end 5, at an inside or lower side of the end of the first forceps arm 2.

The bullet 6 in one of its embodiments is preferably designed to be able to receive and affix a surgical needle pierced therethrough. A material to be used as the bullet 6 is suitably a synthetic material, for example synthetic rubber or other elastomeric material. Advantageously, the bullet 6 together with the end of the arm upon which it is placed define a space between the first arm 2 and the second arm 3 which can be reduced or increased. The fabrication of this is well known to the person skilled in the art and requires no further elucidation.

Figure 2:
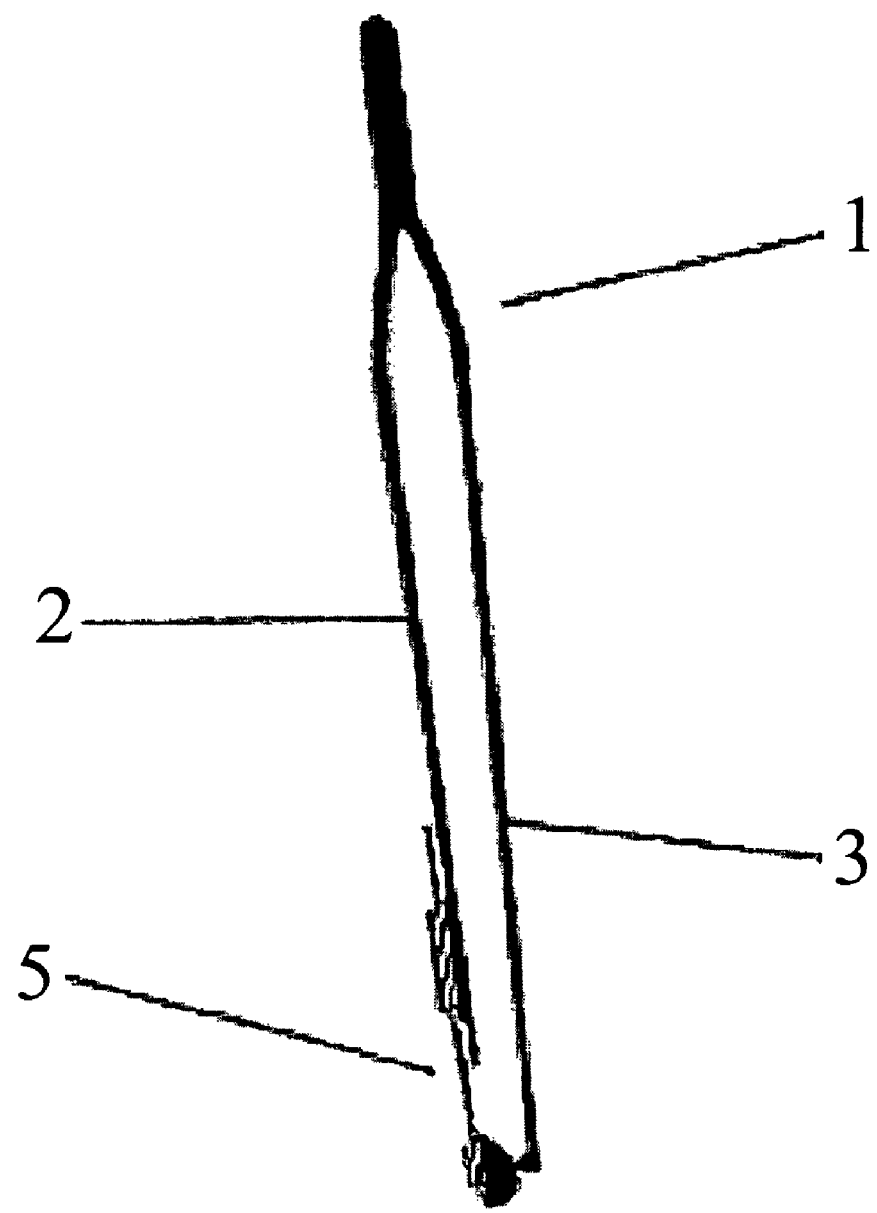
FIG. 2 shows a side elevation of the surgical forceps shown in FIG. 1.

FIG. 2 shows a side elevation of the surgical forceps 1 according to the invention wherein the first forceps arm 2 and the second forceps arm 3 are moved toward each other.

Figure 3:
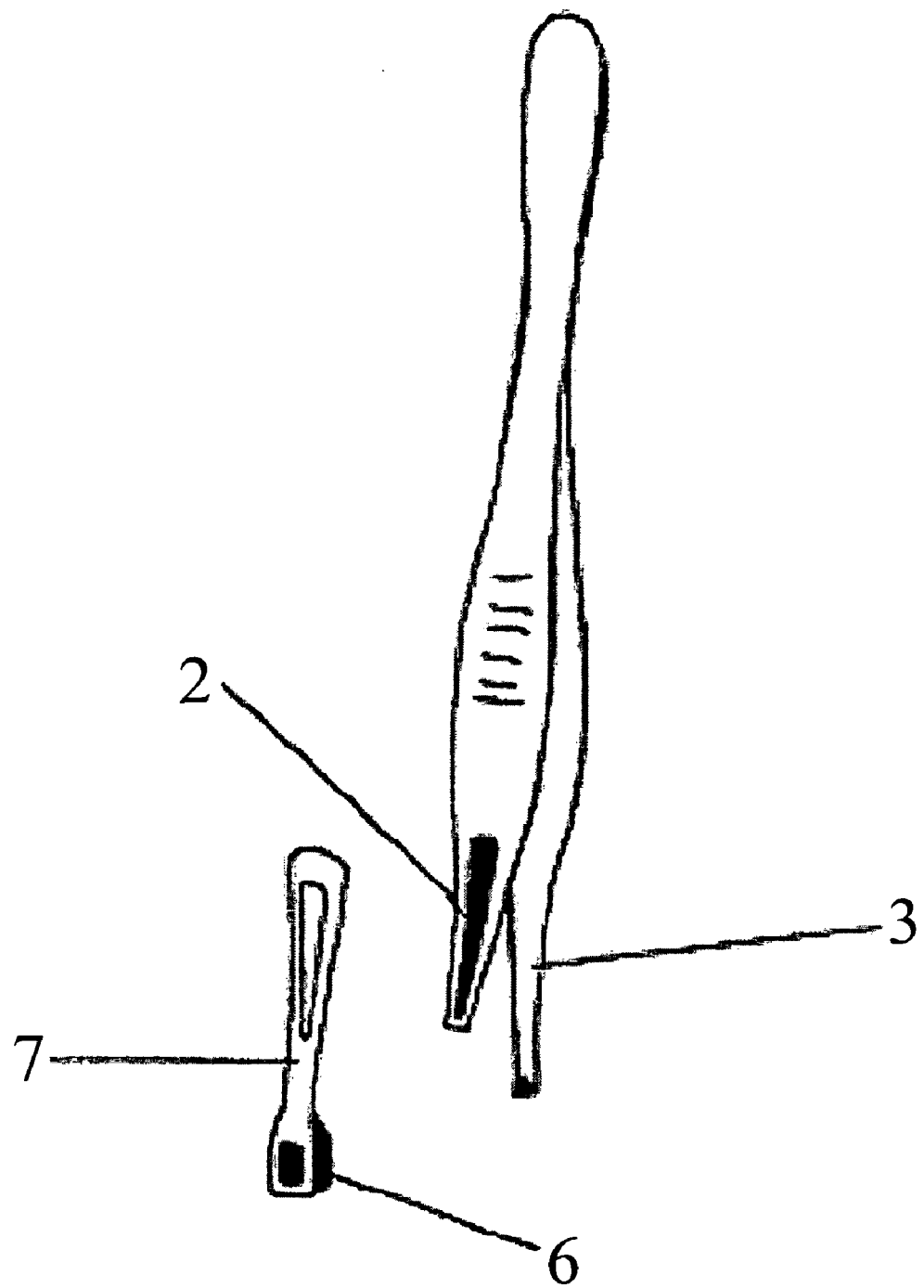
FIG. 3 shows the surgical forceps depicted in FIG. 1 wherein a holder with a bullet is detached from the forceps.

FIG. 3 shows that the bullet 6 is provided on a holder 7 that is detachable from but, as in the illustrated case, can also be detachably placed on the first forceps arm 2. Any means of attachment and detachment may be used including that illustrated in FIG. 3, screw on and off attachment means, clip on, luer-lock and others.

The use of the surgical forceps 1 according to the invention may conveniently be explained by way of a series of successive steps illustrated in the FIGS. 4-7, showing the use of the surgical forceps 1 according to the invention for suturing tissue.

Figure 4:
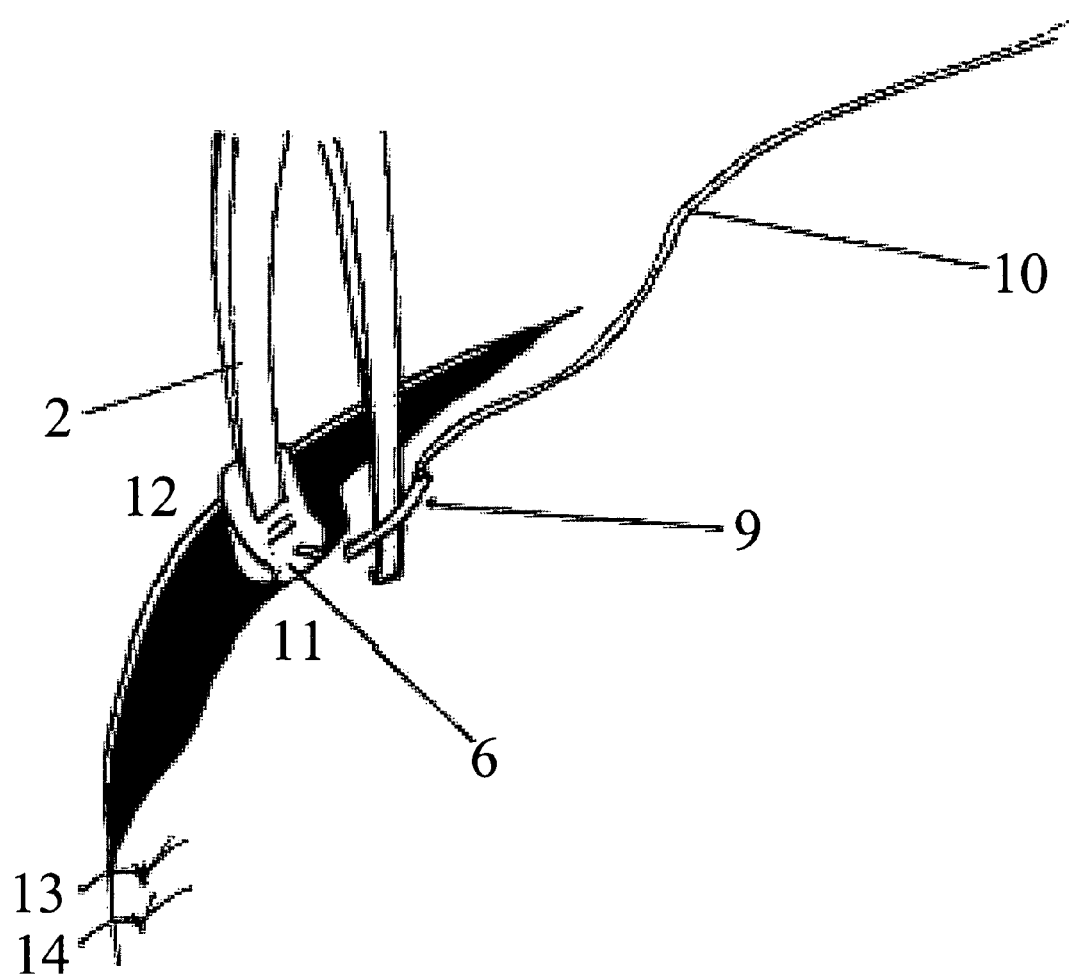
FIGS. 4-7 show several successive stages of using the surgical forceps according to the invention while suturing tissue.

FIG. 4 shows a first step, wherein by means of a needle-holding tool (not shown) a surgical needle 9, attached to which is a suture 10, pierces a first tissue portion 11 in order to join this first tissue portion 11 with a second tissue portion 12.

Reference numerals 13 and 14 indicate two sutures made previously through the first and second tissue portions 11 and 12.

FIG. 4 shows clearly that the first forceps arm 2, which at the inside distal end is provided with a bullet 6, serves to support the first tissue portion 11 through which the suture 10 is passed. In this way the surgical forceps 1 according to the invention are able to effectively support the first tissue portion 11 so as to avoid damage to this first tissue portion 11, while simultaneously a point of the surgical needle 9 is able to pass into the bullet 6 in order to receive and affix the surgical needle 9 therein.

Figure 5:
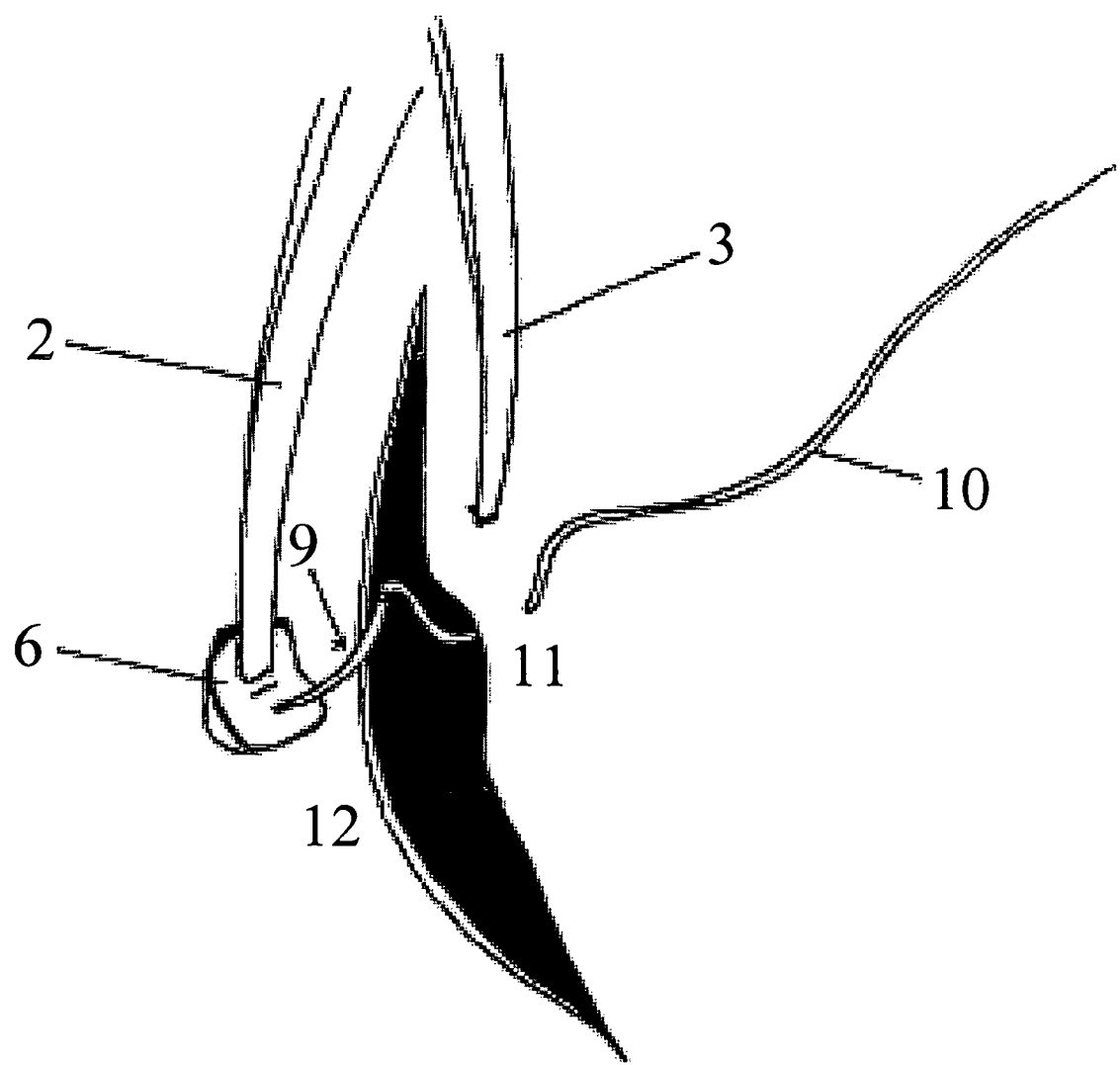

FIG. 5 subsequently shows that the surgical needle 9 can be passed further through the first tissue portion 11 by employing the surgical forceps 1 in accordance with the invention.

Figure 6:
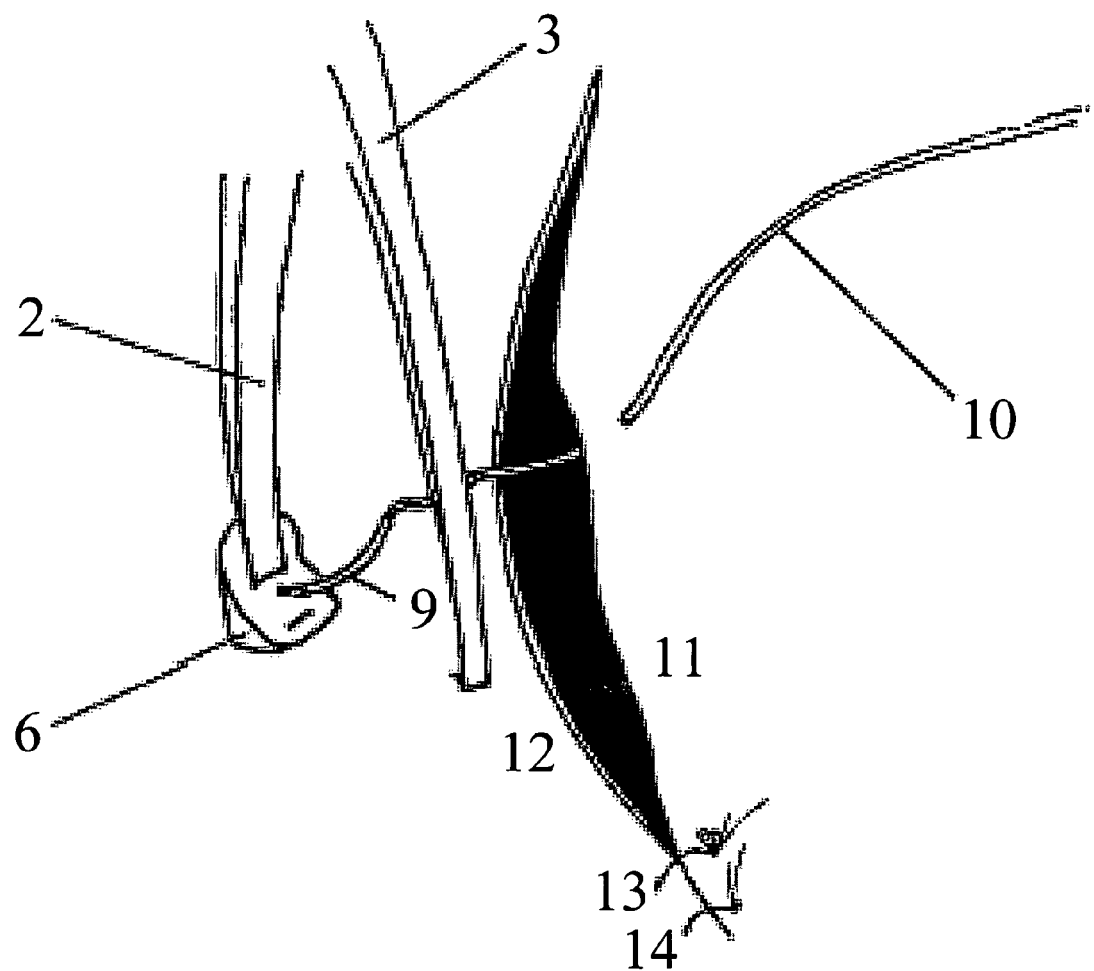
Figure 7:
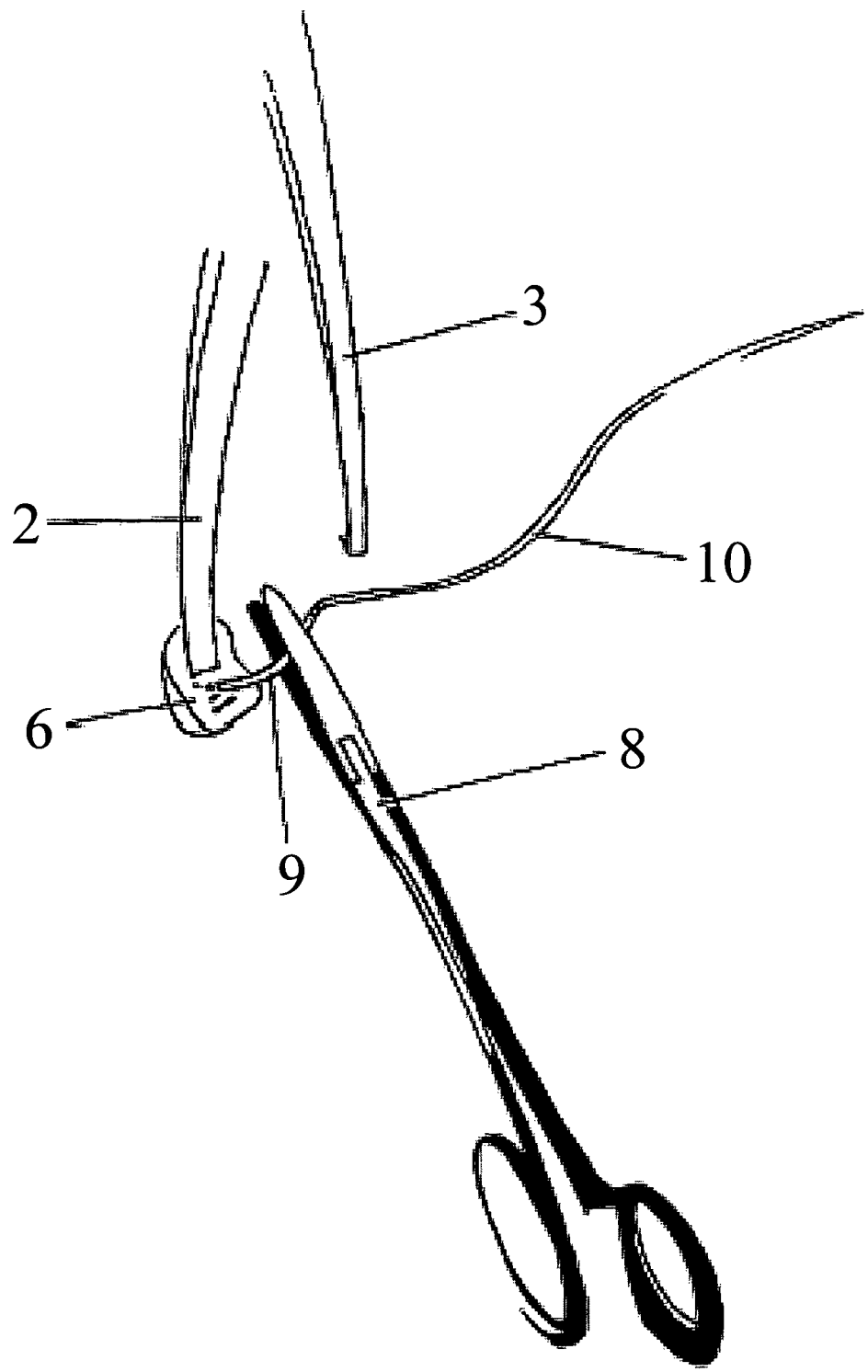

FIG. 6 subsequently shows that the surgical needle 9, with the suture 10 attached thereto, is in an advanced stage of its passage through the first tissue portion 11 and as FIG. 7 further shows, that the surgical needle 9 thus becomes available again for manipulation by using a needle-holding tool 8.

FIGS. 8-10 show embodiments of various mechanisms by which the bullet 6 may receive and affix a surgical needle 9. FIG. 8 shows a wire mesh embodiment of the bullet 6 wherein a tightly woven mesh with wires 15 that can slide in relation to each other, with at some intervals no sliding knots between wires. The surgical needle 9 is inserted in one of the pores 16 resulting in displacement of the wires until a non-moving corner 17 is encountered. The interval of the non-moving corner 17 assists in the grip on the needle 9.

FIG. 9 shows a "form lock" embodiment wherein a bullet 6 is comprised of a synthetic rubber material with a hollow core. The bullet may be of any shape. The act of inserting a surgical needle 9 through the first layer 18 and subsequently through an open space 19 and then through a second layer 20 of the bullet 6 causes a deformation of the bullet 6. The physical dynamics of the bullet 6 trying to return to its neutral shape, due to its material memory, causes increased pressure to be borne on the needle 9, thereby increasing the grip the bullet 6 has on the needle 9.

FIG. 10 shows a "saloon doors" embodiment of the bullet 6 wherein the surgical needle 9 is stuck between two pieces of material or flaps 21 that have a very narrow slit 22 in between. The needle 9 is guided to go between the two flaps 21, resulting in "opening the saloon doors." When the forceps are manipulated to pull the surgical needle 9 out of the tissue, the flaps 21 close, resulting in a grip on the surgical needle 9 because of the additional space the needle 9 occupies between the flaps 21. The greater the pulling force applied, the stronger the grip on the needle 9 because of the friction between the needle 9 on the flaps 21 forces the flaps to close further. After the needle 9 is pulled through the tissue, the needle 9 is released by pulling or pushing it in the direction the flaps 21 open.

The remaining figures address the potential problem encountered in suturing in which the surgeon wants to pull the needle (that is affixed to the bullet) through the tissue. In order to do so without harming the tissue, the surgeon will want to guide the forceps following the curvature of the needle. By doing so, the arm opposite the arm with the flexible material can touch or even get stuck in the tissue.

FIGS. 11-13 illustrate the surgical forceps with a double hinge mechanism. In FIG. 11, the instrument is comprised of a longer first arm 2 and a shorter second arm 3 with a hinge mechanism that includes a lever 23 and a hinge 24 fixed to the distal end of the second arm 3. When combined with the lever 23, the distal end of lever 23 contacts the distal end of the first arm 2 when the instrument is in the closed position.

FIG. 12 shows the surgical forceps 1 with the hinge mechanism comprised of a lever 23 and a hinge 24 in the open position. A spring 25 may be used to enforce the open position when the forceps are not engaged.

FIG. 13 shows the surgical forceps 1 in both the open and closed positions. Note the difference in length of the second arm 3 combined with the lever 23 along the axis of the forceps when in open and closed positions. In the open position, the lever 23 is out of the way when making a circular motion with the forceps to pull a needle (not shown) through tissue along the curvature of the needle thereby avoiding unwanted contact with and/or damage to the tissue.

FIG. 14 shows the spring enforced sliding arm embodiment of the surgical forceps 1 wherein the second arm 3 is shorter than the first arm 2. The second arm 3 has attached to it at the distal end a sliding lever 26. A spring 27 is fixed to a medial region 28 of the first arm 2 and the sliding lever 26 such that it makes the distal end of the sliding lever 26 slide in the proximal direction when the forceps are in the open position. When the forceps are closed, the sliding lever 26 slides towards the distal end of the instrument to enable sufficient grip of the first tissue portion 11 to be sutured.

FIG. 15 illustrates the flipping bullet embodiment of the invention wherein a short arm 29 to which a bullet 6 is attached is fixed at the distal end of the first arm 2 by a hinge 30. The first arm 2 is shorter than the second arm 3, but in the closed position, the distal end of the short arm 29 to which the bullet 6 is attached touches the distal end of the second arm 3. Spring-forced movement of the hinge 30 that the surgeon can manipulate flips the short arm 29 away from the longer second arm 3 of the forceps and allows the surgeon to pull the surgical needle (not shown) through, along the natural needle path, without damaging the tissue.

FIG. 16 illustrates the accentric axis embodiment of the invention wherein an elliptical hinge mechanism 31 in which the point of rotation in the proximal end of the forceps makes a translating movement at the same time as the rotating movement takes place. Under this design, when the forceps are in the closed position, the distal end of the second arm 3 extends such that it meets the distal end of the first arm 2. In the open position, the elliptical hinge mechanism 31 shortens the second arm 3', thereby avoiding damage to the tissue.

FIG. 17 illustrates the double spring embodiment of the invention wherein the second arm 3 that is opposite the bullet 6 is retracted and extended by a first spring 32 that holds the first arm 2 and second arm 3 apart in the open position in which the second arm 3 is shorter than the first arm 2. When the first spring 32 is engaged and the distal ends of the two arms are brought together, a second spring 33 located at the proximal end 4 of the forceps and fixed to the shorter second arm 3 is also engaged and extends the shorter second arm 3 such that the distal ends of the first arm 2 and second arm 3 meet when the instrument is in the closed position.

It is also apparent that the forceps according to the present invention is not only useful in "open surgery," its advantages may be exploited in endoscopic surgical procedures or in combination with other endoscopic tools wherein a single arm with a bullet attached at a distal end is employed. The bullet simultaneously supports the tissue to be pierced with a surgical needle and is capable of receiving and affixing the needle thereafter so that the needle can be manipulated with the instrument.

The invention claimed is:
1. A method for suturing tissue using a forceps comprising:
(a) a first arm and a second arm that are connected at a proximal end and are moveable toward and away from one another at a distal end and which define a space between said arms which can be reduced or increased; and
(b) a bullet, placed at the distal end of said first arm, at an inside of the distal end of said first arm, to receive and affix a surgical needle while gripping the tissue, the method
comprising the steps of securing and supporting a first area of tissue to be sutured by gripping the tissue with said distal end of said forceps, securing said surgical needle and a suture material attached thereto with a needle holding tool, piercing said first area of tissue to be sutured with said surgical needle using said bullet to support said tissue, passing said surgical needle through said tissue and affixing said surgical needle to said bullet of said forceps while gripping the tissue, releasing said surgical needle from said needle holding tool, releasing said first area of tissue secured by said forceps, guiding the surgical needle with said forceps following a curvature of said surgical needle, and removing said surgical needle from said bullet of said forceps by securing said surgical needle with said needle holding tool.

2. The method of claim 1 wherein said method is repeated on a second area of tissue to be sutured to said first area of tissue whereupon said suture passing through said first area of tissue and second area of tissue is tied in a knot.

3. The method of claim 2 wherein prior to said bullet receiving and affixing said surgical needle, said first and second areas of tissue to be sutured are pierced by said surgical needle in one movement.

4. The method of claim 1 wherein said suture is knotted by a force applied by said needle holding tool pulling on an end of said suture and a second pulling force applied by said forceps to which said surgical needle is affixed.

\* \* \* \* \*